United States Patent [19]

Lee-Huang

[11] Patent Number: 4,568,488

[45] Date of Patent: Feb. 4, 1986

[54] REVERSE IMMUNOAFFINITY CHROMATOGRAPHY PURIFICATION METHOD

[76] Inventor: Sylvia Lee-Huang, 345 E. 69th St., New York, N.Y. 10021

[21] Appl. No.: 570,075

[22] Filed: Jan. 11, 1984

[51] Int. Cl.$^4$ .................. C01G 7/00; A61K 37/24; A61K 35/22

[52] U.S. Cl. .................. 260/112 R; 260/112 B; 424/99; 424/100; 424/85; 424/88; 435/226; 514/21

[58] Field of Search .................. 260/112 R, 112 B; 424/99, 100, 85, 88, 177; 435/226; 514/21

[56] References Cited

U.S. PATENT DOCUMENTS

| | | | |
|---|---|---|---|
| 3,994,870 | 11/1976 | Neurath et al. | 260/112 B |
| 4,172,827 | 10/1979 | Giaever | 260/112 R |
| 4,252,902 | 2/1981 | Fujii et al. | 435/226 X |
| 4,254,095 | 3/1981 | Fisher et al. | 424/88 X |
| 4,289,689 | 9/1981 | Friesen et al. | 424/85 X |
| 4,289,690 | 9/1981 | Pestka et al. | 260/112 R |
| 4,303,650 | 12/1981 | Takezawa et al. | 424/177 |
| 4,332,717 | 6/1982 | Kanaoka et al. | 260/112 R |
| 4,361,509 | 11/1982 | Zimmerman et al. | 260/112 B |
| 4,377,513 | 3/1983 | Sugimoto et al. | 260/112 R |
| 4,397,840 | 8/1983 | Takezawa et al. | 424/177 X |
| 4,465,624 | 8/1984 | Chiba et al. | 260/112 R |

OTHER PUBLICATIONS

J. of Biol. Chem. 252, 5558-5564 (1977), Miyake et al.
Experientia, vol. 29, p. 758, (1973), Sieber et al.
Proc. Acad. Sci. USA, 74, 4633-4635 (1977), Spivak et al.
Blood, 56, No. 4, 620-624 (1980), Lee-Huang.
Blood, 52, No. 6, 1178-1188, Spivak et al.
J. Lab. Clin. Med.–vol. 93, 40-53 (1979), Tuddenham et al.
J. Lab. Clin. Med. vol. 101, 736-746 (1983, May), Rotblats et al.
Proc. Natl. Acad. Sci. USA, vol. 79, 1648-1652 (1982), Fulcher et al.
Scientific American, 66-74 (1980), Milstein, vol. 243.

*Primary Examiner*—Howard E. Schain
*Attorney, Agent, or Firm*—Darby & Darby

[57] ABSTRACT

One aspect of the present invention relates to a method for the purification of a protein component of a biological fluid, said method comprising: raising antibodies to impurities commonly present in crude preparations of said components; preparing an immunoadsorbent complex by linking said antibodies to a solid adsorbent suitable for use in column chromatography; processing a preparation of said component containing impurities through a chromatography column containing said immunoadsorbent, thereby causing selective adsorption of said impurities and exclusion of said component in the effluent; and recovering said purified component from said effluent. Another aspect of this invention is directed to human urinary erythropoietin purified by the above method.

12 Claims, 4 Drawing Figures

1

1   2

REVERSE IMMUNOAFFINITY CHROMATOGRAPHY PURIFICATION METHOD

The United States Government has rights to this invention by virtue of grant No. R01-HL21683 by the National Institute of Health, Bethesda, Maryland.

FIELD OF THE INVENTION

The present invention relates to a method for purifying a protein component of a biological fluid. More specifically, the present invention relates to a novel immunoaffinity chromatographic method for purifying a protein that could not be adequately purified by conventional immunoaffinity chromatographic techniques. The invention is particularly suitable for purifying erythropoietin, but is equally applicable to purification of a great variety of weakly immunogenic proteins, glycoproteins, hormones and enzymes which are difficult to resolve from their contaminants.

BACKGROUND OF THE INVENTION

Human erythropoietin (Ep) is an acidic glycoprotein hormone with an apparent molecular weight of 34,000 daltons. It is the primary regulator of erythrocyte (red blood cell) production. Its known major functions are promotion of erythroid differentiation and initiation of hemoglobin synthesis, but it may also be involved in stimulation of limited proliferation of immature erythrocyte precursors.

An understanding of the mode of Ep action is of considerable biological importance. Not only would it serve as a useful model for studying the differentiation and development of mammalian cells, but it would also be of great value in the diagnosis and treatment of anemias. Although much research has been directed to this area, progress has been slow due in part to the lack of pure Ep. This is caused both by scant availability of starting materials and by difficulties in purification.

Unavailability of sufficient quantities of pure Ep has also hindered the development of Ep-specific monoclonal antibodies using hybridoma techniques and the use of recombinant DNA technology in the molecular cloning of Ep genes and the production of hybrid cells which would produce human Ep gene products.

Ep circulates in the plasma space and is excreted in the urine at very low concentrations under normal conditions. However, under anemic or anoxic stress, Ep levels in the urine may increase considerably. Thus, urine from severely anemic patients (e.g., patients with aplastic anemia, leukemia, or various hemoglobinopathies) have been the sole source of human Ep, to date. Not all anemic patients, however, exhibit increased urinary Ep levels. Accordingly, monitoring of patients is necessary to determine whether their urine will be useful as a source of Ep. Moreover, once a patient responds to a therapeutic treatment, his or her urinary Ep levels change rapidly, making it necessary to seek a new Ep source. In addition, Ep must be purified from the urine before it can be further used.

Many attempts have been made in various laboratories to purify human Ep. The major difficulties with these attempts have been the limited supply of starting material, and the incomplete resolution of Ep from urinary contaminants. Early attempts to fractionate with organic solvents and salts resulted in a distribution of activity in several fractions. The fractions of higher activity have often been obtained in low yield. Conventional chromatographic techniques have been similarly limited in efficiency. Several purification procedures have been reported. One such procedure described by Espada, I., et al, *Purification de Erythropoietina Urinaria Humana,* Acta Physiol., Lat. Am. 10:122–129, 1970, involved a ten-step operation; briefly: (1) benzoic acid adsorption, (2) protein precipitation, (3) ethanol precipitation, (4) heat treatment, (5) Diethylaminoethyl(DEAE)-cellulose chromatography, (6) hydroxylapatite adsorption, (7) 2nd DEAE-cellulose chromatography, (8), (9), and (10) 1st, 2nd, and 3rd Sephadex G100 gel filtration. This procedure gave a 323-fold purification with 18.5% yield. The specific activity increased from 25 units/mg of protein in the starting material to 8086 units/mg of protein in the final product (units as defined below). According to these workers, this procedure is efficient only when applied to large amounts of raw material and when the starting material has an Ep titer of 20 units/mg or higher. The starting material used in the above-described work was urine collected in Argentina from patients afflicted with anemia due to hookworm infection.

Another procedure reported by Miyake, T, et al, *Purification of Human Erythropoietin,* J. Biol. Chem. 252:5558–5564, 1977, consisted of initial desalting on Sephadex G25, followed by seven steps, namely: (1) DEAE batch elution, (2) p-aminosalicylate treatment and phenol extraction, (3) ethanol fractionation, (4) DEAE agarose column chromatography, (5) sulfopropyl-Sephadex chromatography, (6) Sephadex G100 gel filtration, and (7) hydroxylapatite adsorption. Again, this procedure requires large amounts of starting sample with high initial specific activity. Seven million units with an exceptionally high starting Ep titer of 91 units/mg of protein were processed all at once. The final product had a specific activity of 70,400 units/mg of protein. This represented a purification factor of 930 with 21% yield.

High Ep titer urine from aplastic anemic patients of unknown origin collected in Kumanoto City, Japan was used as the starting material. In the United States, however, it is impossible to have a large supply of urine of such high Ep titer due to the practice of giving anemic patients blood transfusions. Thus, it is impossible to repeat this procedure on comparable starting material with equivalent Ep titer. Quite different results and much lower specific activity have been obtained when repeating this process on a small scale with low Ep titer urine samples collected in the U.S.A.

Furthermore, each of the above procedures requires constant use of large amounts of benzoic acid and phenol. The former is toxic, and the latter a known mutagen; they are thus deleterious to Ep research goals.

Aside from the problems due to the extremely low initial content of Ep in urine, purification of the hormone is quite difficult to achieve because it is contaminated with many urinary impurities with similar physiochemical properties. Many of the existing purification procedures are based on either conventional charge and size separations, or sugar-specific affinity to lectin derivatives. A simple prior group separation on the basis of a different and independent property, hydrophobicity, proved important for the elimination of contaminating impurities from Ep with similar size and charge as well as similar monosaccharide content. Use of hydrophobic interaction chromatography (HIC) in Ep purification, has been reported by Lee-Huang, S. *A New Preparative Method for Isolation of Human Erythropoietin* with *Hydrophobic Interaction Chromatography,* Blood 56: 620–624, 1980.

Immunoaffinity chromatography is highly specific and effective for the purification of many macromolecules. However, in the absence of sufficient quantities of pure Ep as the immunogen for the production and/or purification of Ep-specific antibodies, the potential of conventional immunoaffinity becomes limited. Even if highly purified Ep is used for the immunization of antibody producing animals, these animals frequently generate large amounts of antibodies against minor contaminants, especially when the main antigen is a weak immunogen, as is the case with Ep. Conventional immunoaffinity chromatography can thus only yield a preparation as pure as the original antigen, since antibodies to the contaminants also immunoabsorb their antigens.

The present invention involves a novel and simple immunoaffinity technique for use in Ep purification. The experimental results showed excellent potential and general applicability of the procedure. This novel procedure is especially well suited for initial processing of crude starting material of moderate Ep titer. In bypassing many steps, unnecessary handling of the sample is eliminated, and the yield is increased accordingly. The present specification includes a description of a systematic investigation of some of the important parameters for high resolution and good recovery. By the combination of HIC, Direct Immunoaffinity chromatography (DIAC), and Reverse Immunoaffinity Chromatography (RIAC) in particular, a purification factor of 35,000 fold with 59% yield has been achieved. The specific activity increased from 0.91 units/mg of protein in the starting material to 32,000 units/mg of protein in the final product. This procedure is simple, rapid, and effective, and is suitable for the processing of low and high Ep titered urine in large or small quantities. Some of the starting material was supplied by the National Heart, Lung, and Blood Institute. Additional urine samples were collected from various hospitals in New York City from patients suffering from disorders including aplastic anemia, hemolytic anemia, leukemia and various hemoglobinopathies.

OBJECTS OF THE INVENTION

Accordingly, it is an object of this invention to provide a method for the purification of proteins, and particularly weakly immunogenic proteins present in biological fluids in minor quantities.

It is another object of this invention to provide a convenient method for the purification of such proteins in high purity and high yield at relatively low cost.

Another object is to provide a method for simple and rapid purification of erythropoietin.

It is a further object of this invention to provide a method for purification of biological fluid protein components which bypasses the need of an initial supply of pure protein and pure antibody of such protein.

It is yet another object of this invention to provide a method for purification of biological fluid protein components with an efficiency not heretofore attainable with prior art methods, while preserving the activity of such proteins.

It is still another object of this invention to prepare highly purified erythropoietin in sufficient quantities for the development of its diagnostic and therapeutic applications.

Another object of this invention, is to prepare purified active erythropoietin from a biological fluid, suitable for use in development of Ep-specific monoclonal antibodies, and in quantities sufficient for such use.

These and other objects of this invention will be apparent to those skilled in the art in light of the present description, appended drawings and accompanying claims.

SUMMARY OF THE INVENTION

One aspect of the present invention relates to a method for the purification of a protein component of a biological fluid, said method comprising:
- raising antibodies to impurities commonly present in crude preparations of said component;
- preparing an immunoadsorbent complex by linking said antibodies to a solid adsorbent suitable for use in column chromatography;
- processing a preparation of said component containing impurities through a chromatography column containing said immunoadsorbent, thereby causing selective adsorption of said impurities and exclusion of said component in the effluent; and
- recovering said purified component from said effluent.

Another aspect of this invention is directed to active human urinary erythropoietin purified by the above method.

BRIEF DESCRIPTION OF THE DRAWING

The present invention is illustrated in the accompanying drawings in which.

DETAILED DESCRIPTION OF THE INVENTION

Figure 1A:
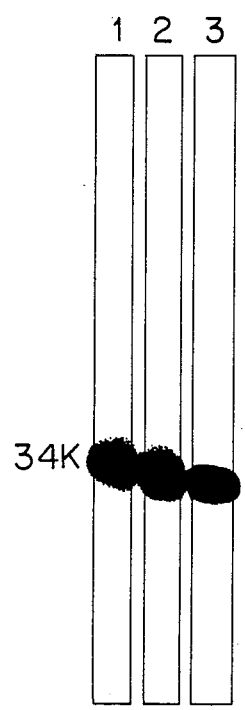
FIG. 1 is a drawing of photographs of: (a) a Sodium dodecyl sulfate polyacrylamide gel electrophoresis (SDS-PAGE) pattern on slab gel, (b) an isoelectric focusing pattern on a disc gel, and (c) an electrophoretic pattern in a non-dissociating disc gel, said patterns being of human urinary Ep purified according to the method of the present invention.

The present invention is described further below with particular reference to purification of erythropoietin from concentrated urine in accordance with preferred embodiments. Such specific description does not detract, however, from the general applicability of the present method to purification of other protein constituents of biological fluids. The method of the present invention may be used in the purification of other weakly immunogenic proteins, glycoproteins, enzymes and hormones, whose contaminants are difficult to remove by conventional methods because, during immunization for the purpose of obtaining antibodies to such proteins, corresponding antibodies to the main antigen and its contaminating impurities are concurrently produced. Of course, as those skilled in the art will readily appreciate, the procedures for the resolution of these antibodies may differ according to the substance to be purified. For example, if the protein desired to be purified is a glycoprotein, purification of antibodies may be carried out on a lectin-glycoprotein column; if it is an enzyme, purification may be conducted on an enzyme substrate analogue-enzyme column; if it is a metal-containing protein, purification may be accomplished on a Thiopropyl-Sepharose-metal-containing protein column, or an iminoacetic acid Sepharose-metal-containing protein column. If it is a sulfhydryl containing protein, an organomercurial Sepharose column may be used, since the organomercurial readily forms a covalent mercaptide with free sulfhydryls. The solid supports mentioned here are not restricted to Sepharose. Agarose or other forms of gel matrix are also appropriate. In addition, the eluant, buffer, and other media used, should be selected in accordance with the affinity characteristics of the substance to be purified and with due consideration given to the differential affinity between its immunospecific and biospecific ligands where applicable, as is well known in the art.

According to the present method, unconcentrated or concentrated urine from severely anemic patients can be used as the raw material. Starting samples, are preferably first centrifuged to eliminate insoluble material and purified preferably by hydrophobic interaction chromatography (HIC), as described by Lee-Huang, S.: *A New Preparative Method for the Isolation of Human Erythropoietin With Hydrophobic Interaction Chromatography,* Blood 56:620–624, 1980, in order to remove the bulk of urinary contaminants and permit more efficient and repeated use of the immunoadsorbents. HIC involves processing of the raw material through a crosslinked neutral gel chromatographic column wherein the gel contains a hydrophobic group. Phenyl-Sepharose CL4B is particularly preferred because it provides a strong yet easily reversible binding with Ep. Octyl-Sepharose may also be used, but Ep elution therefrom is less complete. The specific activity of Ep obtained from this step depends on the potency of the starting material but generally ranges between about 115 and 250 units per mg of protein. The yield is usually about 80%. One unit of Ep is defined as the activity contained in 0.5 mg of the second International Reference Preparation of Human Urinary Erythropoietin (IRP) (obtained from the World Health Organization, International Laboratories of Biological Standards, Hampstead, London, England), or one-tenth of the contents of one ampule of this preparation.

The HIC-purified material can be used as the immunogen to raise antibodies to Ep (hereinafter designated as "Anti-Ep") and its common contaminating impurities (hereinafter designated as "Anti-I"). This can be conveniently performed in a single immunization using antibody-producing laboratory animals. The immunization is carried out in accordance with methods well known in the art and, in the case of Ep or other weak immunogens, it preferably includes several booster injections in addition to the initial injection. Anti-Ep titers are determined by the in vivo exhypoxic polycythemic mouse bioassay described by Camiscoli, J. F. and Gordon, A. S.: *Bioassay and Standardization of Erythropoietin* in Gordon, A. S. (Ed.) *Regulation of Hematopoiesis,* Meredith Corp., New York, 1970 pp 370–396.

Polycythemia is induced in mice by hypobaric hypoxia. In order to keep a high protein concentration and thus stabilize the Ep activity, Ep samples for assay are made up in a buffered albumin solution. Samples are injected into mice posthypoxia, intraperitoneally. Ep activity is measured by its stimulation of $^{59}$Fe incorporation in red blood cells. $^{59}$Fe incorporation is determined in a gamma counter. The results are compared to those obtained using the second IRP from WHO. Anti-Ep titers are determined by assaying for ability to neutralize Ep-stimulated $^{59}$Fe incorporation in red blood cells.

The immunized laboratory animals are then finally bled. Antisera from the bleedings after the last injection are isolated, assayed for anti-Ep titers, and purified by immunoaffinity chromatography to eliminate non-immunoglobulins. The rabbit antisera are processed through a Sepharose 4B column to which goat-(anti-rabbit) Igs have been covalently linked. The non-immunoglobulins are excluded from the column, while the specific Igs are eluted with, e.g., 3M sodium thiocyanate (NaSCN) or 0.2M acetic acid.

The thus obtained specific immunoglobulin preparation is treated to separate Anti-Ep from Anti-I. For this purpose, a highly purified Ep preparation is preferably used. However, the present invention does not require pure Ep for antibody preparation and/or separation. Partially purified Ep (or other partially purified antigen), prepared according to conventional methods, is adequate for carrying out the method of the present invention.

The antibody separation may be preferably accomplished by a new principle and procedure which employs reversible binding of antigen to a supporting matrix and thus permits subsequent recovery of valuable Ep (or other antigen) after it is used in the Anti-Ep (or other antibody) purification, without substantial loss of activity.

The antibody separation procedure utilizes the fact that Wheat germ Lectin-Sepharose 4B (WGLS) columns coated with purified Ep have differential affinity for their biospecific and immunospecific ligands. The procedure involves four steps:

1. Purified Ep is bound to WGLS to produce a WGLS-Ep complex. Ep binds tightly to WGLS due to interaction of its N-acetyl-glucosaminyl residues with the wheat germ lectin.

2. The affinity purified rabbit immunoglobulins are processed through a WGLS-Ep column: Anti-Ep binds to the WGLS-Ep complex, while Anti-I does not, but is excluded in the effluent and set aside for further use. Of course, since the original purified Ep, that was used to coat the WGLS column in Step 1, was not homogeneous, its impurities will also be carried over to the WGLS column of Step 1 and, consequently a small fraction of the Anti-I will bind to the WGLS-Ep column of Step 1. This was the shortcoming of conventional immmunoaffinity techniques which the present invention has overcome, as will be described below. Anti-Ep bound to the WGLS-Ep complex is eluted and preferably processed again through a regenerated WGLS-Ep column to insure complete resolution of Anti-Ep/Anti-I immunoglobulins. The Anti-I-containing eluents from the first and the second separation are pooled and Anti-I are recovered therefrom.

3. Since the affinity between the constituents of the immune complex (Ep-(Anti-Ep)) is lower than the affinity between Ep and the sugar-lectin complex (WGLS- Ep), Anti-Ep from WGLS-Ep-(Anti-Ep) can be selectively eluted using a weak acid or a dissociation reagent. The ability of WGLS to bind Ep both at low pH and under dissociating conditions makes WGLS a useful adsorbent for Anti-Ep purification and at the same time enables recovery of the valuable Ep (see step 4 below). The thus recovered Anti-Ep is separated from the eluent (e.g., by dialysis) lyophilized, and stored frozen for subsequent use.

4. Ep can be recovered from WGLS-Ep, once Anti-Ep has been eluted, by further elution, preferably with N-acetylglucosamine or N,N-diacetylchitobiose. This is not possible under conventional immunoaffinity procedures since, normally, the immunoadsorbent is irreversibly coupled to the supporting matrix and cannot be recovered. When the supply of the antigen (used as the immunoadsorbent) is limited, the recovery of such materials is a very valuable saving. Alternatively, the column of WGLS-Ep can be regenerated and can be reused.

The thus recovered Anti-Ep and Anti-I are separately covalently linked to CNBr-activated Sepharose 4B. The coupling procedure has been generally described by Axen, R. et al "Chemical Coupling of Peptides and Proteins to Polysaccharides by Means of Cyanogen Halides" Nature, 214:1302-1304, 1967. The Sepharose-(Anti-Ep) and Sepharose-(Anti I) so prepared are used in column form for the direct immunoaffinity chromatography (DIAC) and reversed immunoaffinity chromatography (RIAC) purification of Ep.

The Ep purified by HIC is further purified by DIAC on a Sepharose-(Anti-Ep) column. This purification results in exclusion of the majority of contaminants from the column, which are carried off in the effluent, while Ep is retained on the column. It is important to note, however, that at this stage some antibodies to some minor impurities will be present in the Sepharose-(Anti-Ep) column because of the lack of homogeneous Ep in the immunoaffinity purification of the Anti-Ep. This is the intrinsic limitation of any conventional direct immunoaffinity technique.

Ep from the Sepharose-(Anti-Ep) column is eluted with an appropriate buffer. Choice of buffer is important in preserving Ep activity. For example, commonly used immune complex dissociating acidic buffers or chaotropic ions (such as glycine hydrochloride buffer or sodium thiocyanate) inactivate Ep, while simple alkali gives incomplete desorption. The present inventor has found that inclusion of 10-20% of a polarity reducing agent (such as glycerol or another common 1,2-glycol) and a dissociation agent (such as guanidine hydrochloride or urea) in an alkaline eluant (such as NaOH) facilitates effective release of Ep from the immunoadsorbent while preserving Ep activity. Preferred are ethylene glycol and guanidine hydrochloride, which can be easily removed and which appear to have no detrimental effect on Ep activity.

The thus eluted Ep is dialyzed (preferably immediately and thoroughly) against water and sodium phosphate buffer. Under these conditions, DIAC is very efficient, offering a high purification factor (usually about 169-fold over HIC) and a high yield (usually about 80% or higher). However, the main limitation of DIAC is the impurities in the original Ep preparation. The antibodies against these impurities are carried over in the purification system and immunoadsorb their antigens in the Sepharose-(Anti-Ep) column. As a consequence, the purity of the DIAC product cannot exceed that of the original Ep used in preparation of the WGLS column (Step 1) for antibody purification.

At this point further purification is accomplished with another Sepharose column coupled with Anti-I. While Anti-Ep contains only a minor fraction of antibodies to the impurities, Anti-I consists of the bulk of these antibodies. Thus, the Sepharose-(Anti-I) column will be able to provide sufficient antibody sites to bind substantially all the impurities contained in the DIAC-purified Ep.

Upon loading DIAC-purified Ep onto a Sepharose-(Anti-I) column, the trace impurities are retained in the column due to the formation of specific immune complexes with their corresponding antibodies, which are present in great excess on the column, whereas pure Ep is selectively excluded in the effluent. This step affords preparation of Ep which is purer than the original antigen. Such efficiency is not attainable with other conventional immunoaffinity techniques. This immunoaffinity chromatography step wherein the impurities are bound to their antibodies, while the valuable protein is excluded in the effluent, is referred to as Reverse Immunoaffinity Chromatography (RIAC).

The impurities removed in the reverse immunoaffinity step are a constant set of residual urinary contaminants; and they have been copurified with Ep in many separation techniques, and are therefore fairly uniform from batch to batch. Thus, crude urine from a source different from that employed to generate the antisera can be effectively purified by the HIC-DIAC-RIAC procedure. The amount of Anti-I required for immunoadsorption of these minor impurities of DIAC-purified Ep is small relative to the total capacity of the Sepharose-(Anti I) column. Furthermore, since reverse immunoaffinity chromatography immunoadsorbs only the contaminating impurities, no desorption of Ep is required, thus minimizing manipulation of valuable samples and increasing yield accordingly. The impurities retained on the column can be subsequently dissociated from the immunoadsorbent by eluting with an appropriate acidic eluent. The column is thus regenerated and ready for subsequent use.

The DIAC-RIAC purified Ep can be tested for homogeneity by attempting further purification using conventional purification techniques (preferably chromatographic techniques and/or gel filtration), and assayed for biological activity.

The DIAC-RIAC purified Ep is further tested for homogeneity and characterized by electrophoretic techniques, such as gel electrophoresis, isoelectric focusing, and disc electrophoresis in non-dissociating systems according to well-known methods described by: (a) Laemmli, U. K.: Cleavage of Structural Proteins During the Assembly of the Head of Bacteriophage T4, Nature 227: 680-685, 1970; (b) Catsimpoolas, N. et al (Ed.); Biological and Biomedical Application of Isoelectric Focusing, New York, Plenum Press, 1977, and (c) Davis, B. J.: Disc Electrophoresis-II: Method and Application to Human Serum Protein, Ann. N.Y. Acad. Sci. 121:404-427, 1964.

The following examples serve further to illustrate the present invention, but not to limit its scope.

Materials: Phenyl-Sepharose CL4B, ConA-Sepharose 4B, Wheat germ Lectin-Sepharose 6MB, CNBr Activated Sepharose 4B Sephadex G100 were obtained from Pharmacia Laboratories, Inc., (Piscataway, N. J.) Guanidine hydrochloride (ultra-pure) was obtained from Schwartz-Mann Biochemicals (Spring

EXAMPLE 1

Initial purification of Ep

Urine from selected patients with elevated Ep titers (as determined by the exhypoxic polycythemic mouse bioassay, see below) was obtained from the National Heart, Blood and Lung Institute as well as from physicians in several hospitals in New York City. The patients suffered from disorders including aplastic and/or hemolytic anemia, leukemia, and various forms of hemoglobinopathies.

The starting urine sample was first concentrated by an Amicon DC-2 concentrator/dialyzer (Amicon Corp., Lexington, Mass.) using a H1 DP10 hollow fiber cartridge (10,000 molecular weight exclusion) in order to remove low molecular weight contaminants while simultaneously concentrating. The flow rate of the effluent was initially adjusted to 50 ml/min. The concentrates were dialyzed against distilled water in the same apparatus. The dialyzed samples were then lyophilized and stored in sterile containers at −70° C. Between 130 and 160% of Ep activity was routinely recovered by this process, suggesting that Ep inhibitors with molecular weights less than 10,000 are present in the crude urine, and that they are removed by the H1DP10 hollow fiber.

The concentrates were then processed by HIC on a Phenyl-Sepharose CL4B (PS) column. Generally about 3,000 to 6,150 units of pooled lyophilized urine concentrate were dissolved in 34 ml of the starting buffer (10 mM sodium phosphate/ 4 M NaCl, pH 6.8) by gentle stirring. Any insoluble material was removed by centrifugation at 10,000×g for 30 min. The clear supernatant solution was loaded onto a PS column (2.5×81.5 cm, bed volume 400 ml) previously fully equilibrated with the same starting buffer (by matching of the buffer refractive index to that of the column effluent). 25 ml fractions were collected at a flow rate of 1.5 ml/min. Unbound impurities were washed with the buffer until effluent absorbance at 280 nm ($A_{280\ nm}$) was zero. The column was then eluted with 10 mM sodium phosphate saline buffer (0.5 M NaCl; pH 7.1) to further eliminate urinary contaminants. Ep activity was eluted with 10 mM NaOH containing 20% ethylene glycol and 4M guanidine hydrochloride. The fractions showing Ep activity were pooled. The resulting solution was concentrated by ultrafiltration using an Amicon YM10 membrane. The concentrated sample was dialyzed against PBS (5 mM sodium phosphate containing 0.15 M NaCl) to remove residual guanidine hydrochloride.

Approximately 204 mg of product was obtained from the pooled fractions of every ten PS columns, with a mean specific activity of 124 units per mg. representing 136-fold of purification with 82% yield. This material was stored at −70° C., until sufficient quantities were accumulated for the following usages: it was used as a source of partially purified Ep (Example 3) for antibody purification (Example 4) and as a source for purification according to the present method (Example 6 et. seq.). A particular sample containing 240 units of Ep per mg of protein was used for immunization, described in Example 2 below.

EXAMPLE 2

Immunization of Antibody Producing Animals

Female New Zealand white rabbits (2–2.5 kg initial body weight) were used for immunization. The sample selected from Example 1 (5 mg/ml, 240 u/mg) was emulsified with an equal volume of Freund's adjuvant (obtained from Difco Laboratories, Detroit, Mich.) either complete for primary injection or incomplete for booster injections. One ml of this mixture was injected subcutaneously at multiple sites each time. Booster injections (a total of 3) were given every six weeks and the rabbits were bled two weeks after each boost. A total dose of 2400 units of Ep were given to each animal from the primary and booster injections. Anti-Ep titers were determined by the in vivo exhypoxic polycythemic mouse bioassay, as follows:

CF-1 virgin female mice (22–25 g body weight) from Charles River Laboratories (Boston, Mass.) were used. The animals were exposed to 0.4 atm for 219 hrs (19 hr/day) in a decompression chamber to induce hypobaric hypoxia. Ep and Anti-Ep samples (0.5 ml/injection) were made up in a solution of 0.5% albumin in 0.15 M NaCl and injected intraperitoneally 72 hrs posthypoxia. Antisera were added to Ep samples in various amounts and incubated at 37° C. for 2 hours and then 4° C. overnight before injection. An amount of 0.5μ Ci $^{59}FeCl_3$ in 0.1 ml of saline/albumin was administered to the mice intravenously on the fifth day. Ep activity was measured by its stimulation of $^{59}Fe$ incorporation into the circulating red cells (obtained by cardiac puncture) 48 hr after $^{59}Fe$ injection. Differences in Ep activity observed in mice injected with Ep-antibody mixtures provided a measure of Anti-Ep activity. Percent incorporation of $^{59}Fe$ was determined on 0.5 ml of blood sample in a Beckman Gamma 4000 counter (Beckman, Inc., Palo Alto, Calif.). The second International Reference Preparation of Human Urinary Ep (WHO) was used as a standard. Ep potency was expressed in units per mg of protein. Hematocrit factors were determined in duplicates by the microhematocrit method, using an Autocrit II centrifuge from Clay Adams Division, Becton Dickinson and Company (Parsippany, N. J.) Results from animals with a hematocrit factor of less than 0.52 were discarded. Dose level means were based on quadruplicates.

Anti-Ep content of the antisera ranged from 10–20 units per ml after the first boost and rose to 100–200 units per ml after the last boost.

Blood samples were obtained from the ear vein and allowed to clot at 4° C. for 30 minutes. The antiserum was collected by centrifugation at 10,000 g for 30 min, and purified by an affinity column (0.9×15 cm, bed volume 9 ml) of goat Anti-rabbit immunoglobulins coupled to Sepharose 4B to eliminate the non-immunoglobulin proteins.

Goat anti-rabbit immunoglobulins (Igs) were obtained from Miles Laboratories (Elkhart, Ind.) and coupled to CNBr activated Sepharose 4B as described in Example 5. The coupled material contained about 25 mg Igs/ml of Sepharose. Ten ml of the rabbit antisera were applied to a 9 ml column of goat Anti-rabbit Igs - Sepharose 4B. The column was washed with PBS and the nonimmunoglobulin proteins were excluded from the column in this fraction. The antibodies bound on the columns were eluted with 0.2M acetic acid. Routinely, 30 to 35 mgs of Igs were obtained per ml of antiserum. The affinity purified rabbit Igs contain both Anti-I and Anti-Ep. They were dialyzed against distilled water, lyophilized and stored frozen at −70° C.

EXAMPLE 3

Purification of Ep for Use in Antibody Purification

The Ep preparation of Example 1 was further purified successively by: lectin affinity chromatography on a Con A-Sepharose column and, subsequently on a Wheat germ Lectin-Sepharose (WGLS) column, followed by adsorption chromatographgy on hydroxylapatite and, finally, gel filtration on Sephadex G100.

(1) Lectin Affinity Chromatography on Con A-Sepharose. The Ep preparation from Example 1 was dialyzed against buffer I (PBS containing 0.1 mM of each $MgCl_2$, $MnCl_2$, and $CaCl_2$, pH 7.1) and applied to a column of Con A-Sepharose 4B which was previously equilibrated with the same buffer. The column was washed with buffer I. Ep activity was recovered in the unretained material. The preferred ratio of mg protein loaded to bed volume (ml) is 1:2.

(2) Lectin Affinity Chromatography on Wheat Germ Lectin-Sepharose. The excluded material from the Con A-Sepharose 4B column was loaded directly onto a WGLS 6MB column (at a 1:1 ratio of mg protein to ml bed volume) which was previously equilibrated with PBS. The column was washed with PBS until the $A_{280\,nm}$ of the effluent reached zero. Ep activity was eluted with buffer II (PBS containing 0.1 M N-acetylglucosamine (NAGA)). The active fractions were pooled and concentrated to 1 ml. The buffer of the sample was then changed to 0.5 mM sodium phosphate buffer, pH 7.1 (buffer III).

(3) Adsorption Chromatography on Hydroxylapatite. The Ep sample from the previous step was loaded onto a hydroxylapatite column, (at a 4:5 ratio of mg protein to ml bed vol) previously equilibrated with buffer III. The column was washed with the same buffer until the $A_{280\,nm}$ of the effluent reached zero. It was subsequently eluted stepwise with varying molarities of sodium phosphate buffers, pH 6.8, and 1 ml fractions were collected. Ep activity was found in the 2 mM eluate. The fractions containing Ep activity were pooled and concentrated to 0.3 ml.

(4) Gel filtration on Sephadex G100. The Ep containing fraction from the previous step was applied to a Sephadex G100 column (0.5 × 100 cm, bed volume 19.6 ml) in buffer IV (2 mM sodium phosphate, pH 7.1). Gel filtration was carried out in the same buffer at a flow rate of 3 ml/hr. Fractions of 0.6 ml were collected and Ep activity was eluted between 0.46 to 0.56 column bed volume. The active fractions were pooled, concentrated, lyophilized and stored frozen at −70° C. for use in Anti-Ep purification as discussed in Example 4.

In summary, the steps described in this Example 3 enabled the production of highly purified Ep. A mean specific activity of 20,535 units/mg of protein was obtained for the final product, corresponding to an overall Ep purification of 22,566 fold. The overall yield ranged from 21% to 36%.

It is important to note that the combination of DIAC and RIAC as described in this patent application would achieve a 35,299-fold overall purification with an overall yield of 59%. This enrichment in Ep yield and improvement in purification cannot be accomplished by previously existing conventional techniques.

The purification method outlined in this Example 3, although preferred, is not essential. Relatively pure Ep, however, would have also been suitable.

EXAMPLE 4

Fractionation of the Antibodies of Example 2

A 2.5 ml column (0.8 ×5 cm) of WGLS was equilibrated with PBS and 1.5 mg of the Ep obtained in Example 3 was loaded onto the column. The flowthrough was recycled six times to ensure complete binding of Ep to WGLS. 140 mg of the purified antisera obtained at the end of Example 2 were dissolved in 4 ml of PBS and applied to the WGLS-Ep column. The column was washed with PBS until $A_{280\,nm}$ reached zero. Anti-I was excluded from the column while Ep-bound Anti-Ep was retained on the column. The effluent, containing Anti-I, was set aside, and Anti-Ep was eluted from the column with 0.2M acetic acid.

The Anti-Ep and Anti-I were recycled separately on a regenerated WGLS-Ep column to ensure maximum resolution. The pooled Anti-Ep fractions (5 mg) and Anti-I fractions (134 mg) were dialyzed separately against 4 mM $NaHCO_3$, pH 8.2, lyophilized and stored at −70° C. until sufficient quantities were accumulated for covalent coupling to Sepharose 4B.

The WGLS-Ep column was washed with 10 column volumes of PBS, and the bound Ep was recovered by eluting the column with 0.1M N-acetylglucosamine (NAGA). The specific activity of the recovered Ep was not detectably different from that of the original Ep loaded onto the WGLS column, indicating that no inactivation had occurred. Alternatively, after washing with PBS, the column may be reused as needed.

EXAMPLE 5

Coupling of antibodies to adsorbent

CNBr-activated Sepharose 4B was acid-swollen in 1 mM HCl for 30 min. at a ratio of 1 g of gel per 300 ml of acid, The swollen gel was then washed on glass filter with 200 ml of 1 mM HCl, six times. The Anti-Ep and Anti-I from Example 4 were then separately dissolved in 0.1 M $NaHCO_3$, pH 8.2, containing 0.5M NaCl to a protein concentration of 25 mg/ml. 10 ml of each was then mixed separately with an equal volume of the swollen gel in a 15 ml polypropylene sterile tube. The mixture was rotated end-over-end on an automatic nutator (American Hospital Supply Corp., Model R485-10 Evanston, ILL.) at 4° C. overnight. To remove the unbound material, the resulting mixture was filtered on glass filter (porosity G3) and washed with the above coupling buffer. The remaining active groups were blocked by reacting with 1M ethanolamine at pH 8.2 for 16 hrs at 4° C. with gentle rotation.

Noncovalently adsorbed proteins were removed by four cycles of washing: each cycle involved washing at pH 4.0 with 0.15M sodium acetate buffer followed by washing at pH 8.2 with 0.1M sodium borate buffer (both buffers containing 0.5M NaCl). Typical coupling by this method yielded 94–96% of coupled protein in both Anti-Ep and Anti-I samples.

EXAMPLE 6

Direct Immunoaffinity Chromatography

Material accumulated from Example 1, in 8 ml of buffer V (0.1M sodium phosphate buffer, pH 7.5) at 25.5 mg/ml containing 25,378 units of Ep was subjected to direct immunoaffinity chromatography (DIAC) on a Sepharose-(Anti-Ep) column (10 ml; 0.9×16 cm) prepared using the appropriate complex of Example 5. The column was washed with the same buffer until $A_{280\ nm}$ of the effluent reached zero. The majority of impurities were excluded from the column and Ep was retained. 2 ml fractions were collected. The bulk of the impurities was excluded in fractions 6-30 (FIG. 3A, peak 1, wherein the continuous line designates absorbance at 280 nM and the broken line designates Ep activity). Ep was eluted with buffer VI (10 mM NaOH containing 20% ethylene glycol and 4M guanidine hydrochloride, pH 10.4), as indicated by the arrow on the Figure. Fractions 126-130 (peak 2 on FIG. 3A) contained Ep. The fractions were dialyzed immediately and thoroughly against water and then buffer V. Each fraction was assayed for activity and its $A_{280}$ nm was measured. The active fractions were pooled and concentrated to about 1 mg/ml for further purification.

EXAMPLE 7

Reverse Immunoaffinity Chromatography

Figures 3A, 3B:
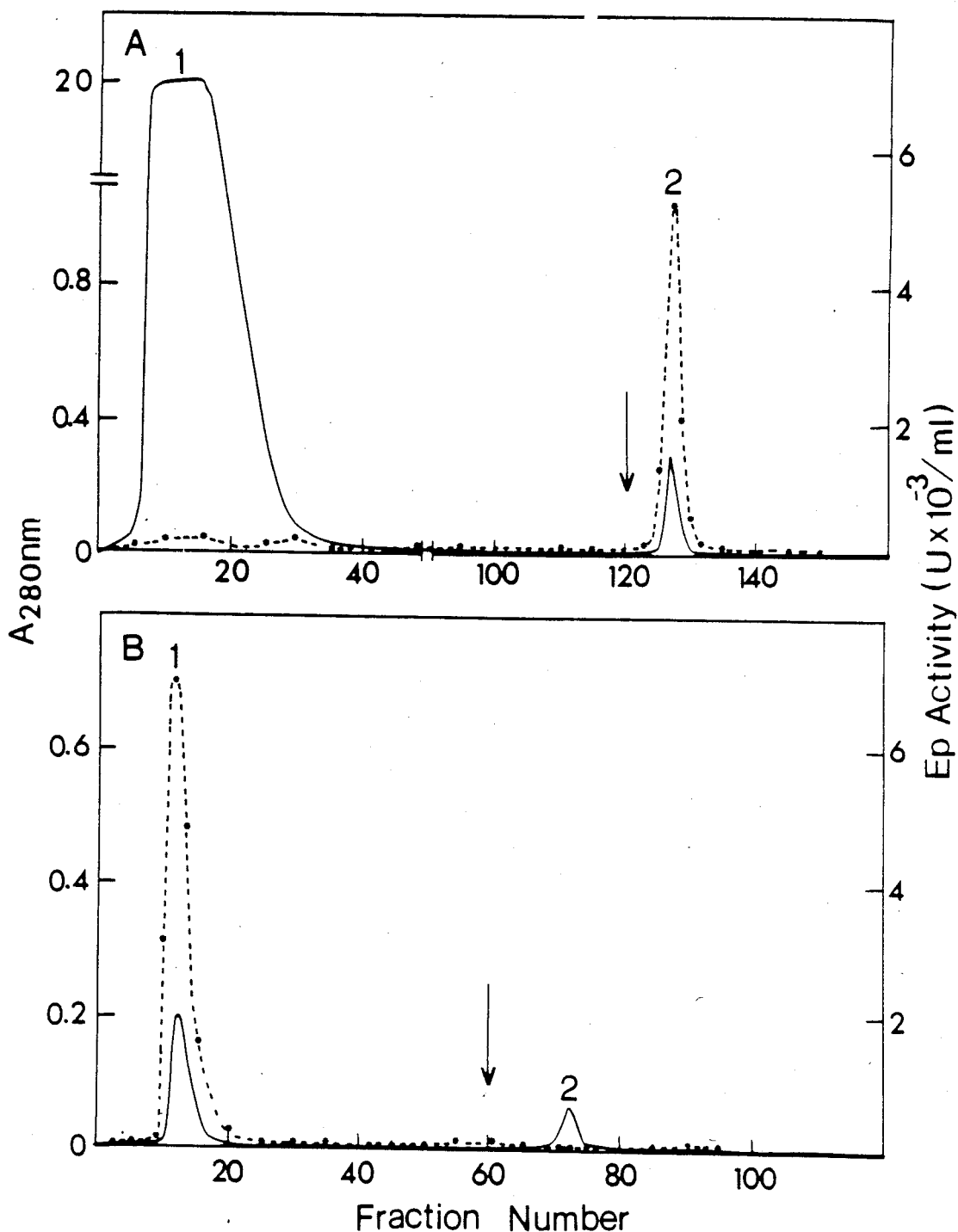
FIG. 3 is a plot of the spectrophotometric absorbance and biological activity pattern of Ep prepared by (a) direct immunoaffinity chromatography (FIG. 3A) and (b) subsequent reverse immunoaffinity chromatography of the (a) product in accordance with the present invention (FIG. 3B).
Figure 4:
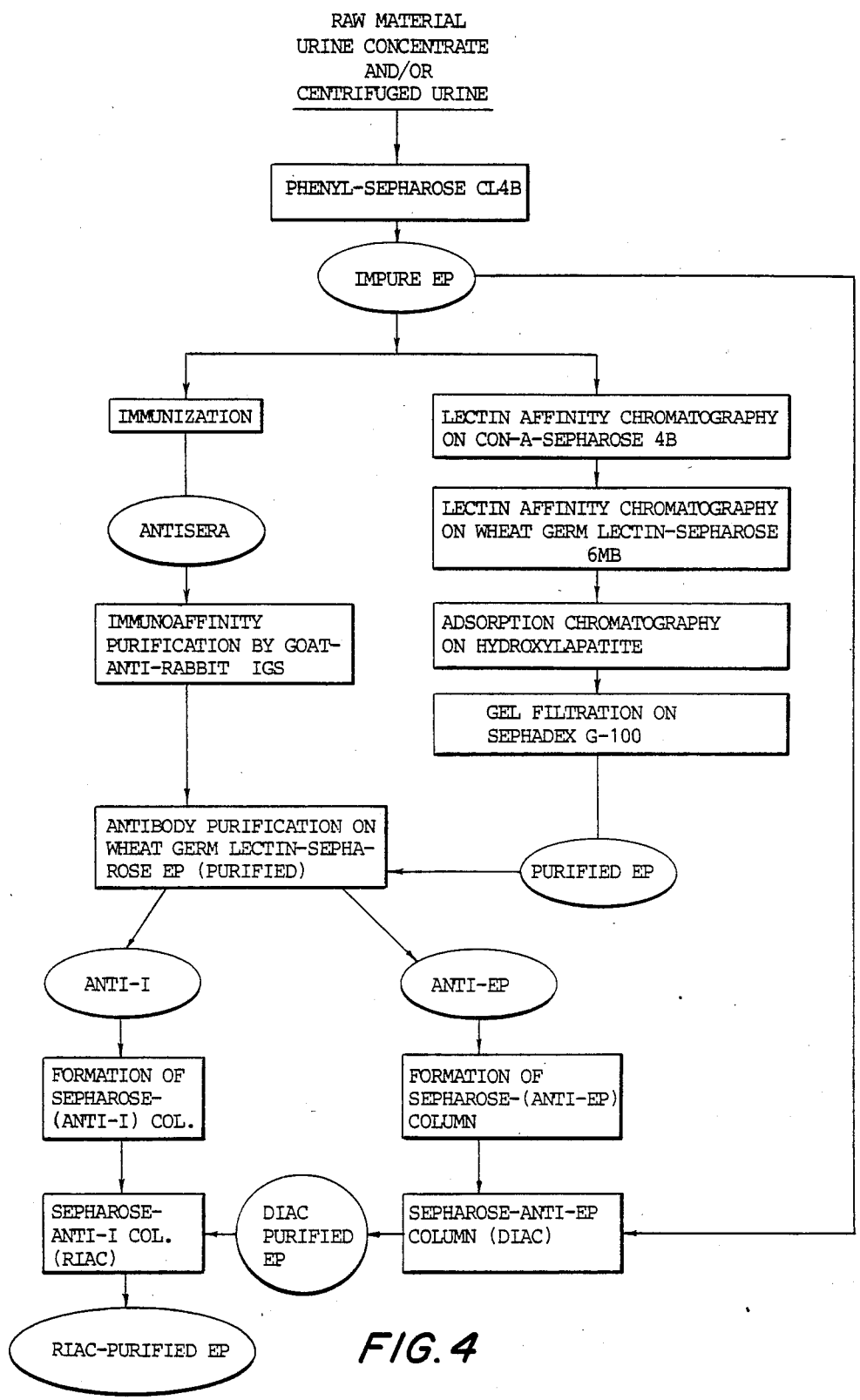
FIG. 4 is a flow chart outlining the various steps of the present invention.

The product of Example 6 (0.99 mg of Ep material/ml buffer V) was applied to the Sepharose-(Anti-I) column (bed vol. 10 ml; 0.9×16 cm) and one ml fractions were collected, (shown in FIG. 3B). The contaminating impurities were adsorbed on the column by their specific antibodies. Pure Ep was obtained in the effluent in fractions 11-18 (peak 1). Each fraction was assayed for Ep activity and monitored for absorbance at 280 nm. The active fractions were pooled and concentrated. This step offered effective and specific removal of the trace residual contaminants. These impurities copurify with Ep and are otherwise difficult to eliminate by conventional separation methods. A final specific activity of 32,122 u/mg was obtained with an overall purification of 35,299 fold and 1.53-fold over the DIAC step. The overall yield was 59% and the yield of the last step was 88% from DIAC.

The column was regenerated with 0.2M acetic acid (as indicated by the arrow in FIG. 3B). The impurities were collected in fractions 70-76 (peak 2). The column was then equilibrated with buffer V, and stored in said buffer containing 0.02% sodium azide at 4° C.

EXAMPLE 8

Test of Homogeneity of DIAC-RIAC Purified Erythropoietin

Protein concentration in samples was determined by a method described in Bradford, M. M. "*A rapid and sensitive method for the quantitation of microgram quantities of protein utilizing the principle of protein-dye binding.*" Anal. Biochem. 72:248-254, 1976.

Further processing of this Example 7-purified Ep material on one or more of hydroxylapatite, Con A-Sepharose, Wheat germ Lectin-Sepharose 6MB, or Sephadex G100 following the procedures described in Example 3, did not increase the specific activity of the Ep. Homogeneity of the DIAC-RIAC-purified Ep was tested by polyacrylamide gel electrophoresis (SDS-PAGE) as follows:

Polyacrylamide gels were prepared according to Laemmli, supra, containing 10% by weight acrylamide, and 0.24% by weight N,N'-bis-methylene acrylamide in 0.375 M Tris-HCl, pH 8.8, sodium dodecyl sulfate (0.1%), tetramethylethylenediamine (0.033%) and ammonium sulfate (0.05%). The Ep preparation was treated with an equal volume of 2× sample buffer containing 0.125 M Tris-HCl, pH 6.8, 4% SDS buffer, 20% glycerol, and 10% 2-mercaptoethanol. Electrophoresis was carried out at a constant voltage of 50 to 100 V for 8 to 4 hours. The gels were fixed and stained with 0.125% coomassie brilliant blue dye in 50% methanol and 10% acetic acid. The results are shown in FIG. 1A. For the sample from Example 7 (40 µg) lane 3, a single band was obtained with a molecular weight of 34,000 daltons. Lanes 1 and 2 are Ep preparations from Examples 3 and 6 (40 µg each).

Figure 1B:

Isoelectric focusing was carried out in 7.5% acrylamide and 0.25% bisacrylamide gel in the presence of 1% carrier ampholytes, pH 3-10. Sulfuric acid (0.2%) and ethylenediamine (0.4%) were used as anodic and cathodic electrolytes, respectively. Electrofocusing was carried out at room temperature. A maximum current of 2 mA/gel was maintained by gradual increase of the voltage up to 200 V. The gels were stained in 0.2% bromophenol blue in ethanol - $H_2O$ - acetic acid (50:45:5) and destained in ethanol - $H_2O$ - acetic acid (30:65:5). A single component with an isoelectric point at 4.1 was obtained (FIG. 1B, 15 µg).

Figure 1C:

Finally, gel electrophoresis in a non-dissociating system was carried out in a 7.5% polyacrylamide (0.24% bisacrylamide) gel in Tris-glycine buffer 0.0426M Tris base (0.0242M glycine, pH 9.6) at a constant current of 2.5 mA per gel column, according to Davis, B. J.: *Disc Electrophoresis - II: Method and Application to Human Serum Proteins,* Am. N.Y. Acad. Sci. 121:404-427, 1964. A single band as seen on FIG. 1C was observed (20 µg sample load).

The purity of Ep prepared in Example 7 was further examined by two other methods: (a) silver stain of the SDS-PAGE sample of Ep, and (b) radioiodination of Ep and autoradiography of the SDS-PAGE sample of $^{125}I$-labeled Ep. These results are shown in FIG. 2 and a single component was detected in each case. These methods are extremely sensitive in detecting microheterogeneity of proteins.

The silver stain procedure involves silver-protein complex formation. Immediately after electrophoresis, the gel was soaked in 400 ml of 40% (v/v) methanol, 10% (v/v) acetic acid for 60 min. and then twice in 400 ml of 10% (v/v) ethanol, 5% (v/v) acetic acid, each time 30 min. Subsequently, the gel was placed in 200 ml of an oxidizer solution for 10 min., followed by a 30 min. wash with 400 ml deionized water. It was then treated with a silver reagent for 30 min., and two changes of a developer solution at 30 sec. and 5 min. The gel was finally developed in fresh developer for the desired amount of time, and development was stopped by the addition of 400 ml of 5% (v/v acetic acid. The oxidizer and developer solutions are products of Bio-Rad Laboratories (Richmond, Calif.).

Radioiodination was carried out using an iodination kit supplied by New England Nuclear Corp. (Boston, Mass.). The kit contains iodination beads coated with lactoperoxidase and glucose oxidase, sodium phosphate buffer, 1% (w/v) β-D-glucose for the generation of hydrogen peroxide by the immobilized glucose oxidase, and carrier free [$^{125}$I]-sodium iodide (1 to 2mCi). Labeling was carried out at room temperature using Ep purified in Example 7. The iodination mixture was subjected to Sephadex G100 gel filtration to remove unincorporated $^{125}$I. A sample of 125I-Ep with 10,000 cpm (1.5 ng) was analyzed by SDS-PAGE under the same conditions as described in FIG. 1. Immediately after electrophoresis, the gel was dried under vacuum and autoradiographed on XAR-5 X-ray film.

Figure 2A:
FIG. 2 is a drawing of photographs of electrophoretic patterns of SDS-PAGE slab gel (a) by silver staining and (b) by autoradiography of $^{125}$I- labeled Ep, said patterns being of human urinary Ep purified according to the present invention.
Figure 2B:
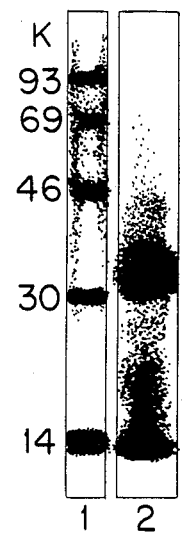

FIG. 2A depicts a silver stained SDS-PAGE pattern: lane 1 shows Ep from Example 7; lane 2 shows mol. weight standards. 2 μg of protein were loaded. FIG. 2B shows an autoradiograph of SDS-PAGE patterns. Lane (1): molecular weight standards (4,000 cpm/band); and lane (2): $^{125}$I-Ep from Example 7 (10,000 cpm).

The results of Ep purification of Examples 1, 6 and 7 are summarized in following Table I:

TABLE 1

| Sample | Purification of Human Erythropoietin | | | | | | |
|---|---|---|---|---|---|---|---|
| | Units (u) | Sp. Activity (u/mg) | Protein (mg) | Yield (%) | | Purification Factor | |
| | | | | Overall | Step | Overall | Step |
| Urine con. | 30,982 | 0.91 | 34,046 | 100 | 100 | 0 | 0 |
| Phenyl-Sepharose CL4B | 25,378 | 124.4 | 204 | 82 | 82 | 137 | 137 |
| DIAC on Sepharose-(Anti-Ep) | 20,773 | 20,983 | 0.99 | 67 | 82 | 23,058 | 169 |
| RIAC on Sepharose-(Anti-I) | 18,309 | 32,122 | 0.57 | 59 | 88 | 35,299 | 1.53 |

These values are based on the 2nd IRP standard (provided by WHO) as mentioned above. It should be noted that at high levels of specific activity, use of the IRP standard may result in an underestimate of the actual specific activity, because the standard itself contains many contaminating activities. For this reason, a purified Ep standard which has been calibrated using the IRP standard at low dose levels is often used. Because it is purer than the IRP, it gives more accurate results than the IRP at high specific activities.

When the activity of Ep prepared in Example 7 was reexamined using purified sheep Ep as a standard, a specific activity of at least 66,000 μ/mg was obtained.

In addition to the specific embodiments described above, numerous other embodiments, variations, modifications and equivalents to the present invention will be apparent to those of ordinary skill in the art in light of the present specification, accompanying drawings and appended claims.

What is claimed is:

1. A method for the purification of a protein component of a biological fluid, said method comprising:
   (a) raising antibodies to all of the antigenic substances other than said protein, commonly present, as impurities, in a crude preparation of said protein, and purifying said antibodies;
   (b) preparing an immunoadsorbent complex by linking said antobodies against said impurities to a solid adsorbent suitable for use in column chromatography;
   (c) processing a preparation of said protein containing said impurities through a chromatography column containing said immuoadsorbent, thereby causing selective adsorption of said impurities in one step and exclusion of said protein in the effluent; and
   (d) recovering said purified protein from said effluent.

2. The method of claim 1 wherein said protein is a weakly immunogenic protein compared to said impurities.

3. The method of claim 1, wherein said protein is present in said biological fluid in minor quantities.

4. The method of claim 1, wherein said protein is selected from the group consisting of weakly immunogenic proteins, glycoproteins, hormones and enzymes present in said biological fluid in minor quantities.

5. The method of claim 1, wherein said biological fluid is selected from the group consisting of human plasma, human urine and human urine concentrate.

6. The method of claim 1, wherein, prior to any of said steps, said biological fluid is subjected to centrifugation to remove insoluble impurities and to chromatography through a hydrophobic gel column to remove the bulk of impurities present in said biological fluid.

7. The method of claim 1, wherein: said step (a) comprises immunizing laboratory animals with crude preparations of said protein, said immunization resulting in simultaneous formation of antibodies to said protein and to all of said impurities, and separating said antigenic impurity antibodies from the antibodies to said protein.

8. The method of claim 7 wherein said step (b) further comprises preparing a second immunoadsorbent complex by linking said antibodies to said protein to a second solid adsorbent suitable for use in column chromatography, and, prior to said step (c), processing said biological fluid through a second chromatography column containing said second immunoadsorbent, thereby causing selective exclusion of the bulk of the impurities contained in said fluid, and employing the fraction of said biological fluid adsorbed in said second column as the preparation of said protein in said step (c).

9. The method of claim 8, wherein said protein is erythropoietin.

10. A method for the purification of a ptorein component of a biological fluid said method comprising:
   (a) concentration said biological fluid;
   (b) centrifuging said concentrate to remove insoluble impurities present in said fluid;
   (c) processing said centrifuged concentrate through a crosslinked neutral gel chromatographic column, said gel containing a hydrophobic group, whereby non-hydrophobic contaminants present in said centrifuged concentrate are exluded and hydrophobic constituents of said centrifuged concentrate are subsequently recovered by elution from said column;
   (d) raising antibodies to all of the antigenic substances other than said protein commonly present, as impurities, in crude preparations of said protein by injecting in laboratory animals a quantity of a curde preparation of said protein sufficient to induce an immune response in said animals, obtaining specific anitsera from said animals and separating said antigenic impurity antibodies from said specific antisera;

(e) linking immunoglobulins of said specific antisera, after separation of said antigenic impurity antibodies therefrom, to a first solid adsorbent suitable for use in column chromatography;

(f) processing said constituents of said concentrate recovered by elution in step (c) through said first immunoadsorbent, whereby the bulk of the impurites remaining in said step (c) concentrate are excluded in the effluent and recovering, as a product, the remaining consitutents of said step (c) concentrate by elution;

(g) linking said antigenic impurity antibodies to a second solid adsorbent support suitable for use in column chromatography;

(h) processing said step (f) product through said second column, wherein the remaining impurites of said protein adsorb to their antibodies and the protein is exclused in the effluent; and (i) recovering said purified protein from said second column effluent.

11. The method of claim 10, wherein said biological fluid is urine.

12. The method of claim 11 wherein said protein is erythropoietin.

* * * * *